(12) United States Patent
Dapolito et al.

(10) Patent No.: US 7,371,248 B2
(45) Date of Patent: May 13, 2008

(54) STEERABLE DISTAL PROTECTION GUIDEWIRE AND METHODS OF USE

(75) Inventors: Steven Dapolito, Brookline, NH (US); Albert H. Dunfee, Byfield, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1002 days.

(21) Appl. No.: 10/685,903

(22) Filed: Oct. 14, 2003

(65) Prior Publication Data

US 2005/0080356 A1    Apr. 14, 2005

(51) Int. Cl.
*A61M 29/00* (2006.01)
*A61F 2/01* (2006.01)

(52) U.S. Cl. ........................ 606/200; 600/585
(58) Field of Classification Search .............. None
See application file for complete search history.

(56) References Cited

U.S. PATENT DOCUMENTS

| | | | |
|---|---|---|---|
| 3,521,620 A | 7/1970 | Cook | |
| 4,456,017 A | 6/1984 | Miles | |
| 4,719,924 A | 1/1988 | Crittenden et al. | |
| 4,723,936 A | 2/1988 | Buchbinder et al. | |
| 5,480,382 A | 1/1996 | Hammerslag et al. | |
| 5,814,064 A * | 9/1998 | Daniel et al. | 606/200 |
| 5,865,800 A | 2/1999 | Mirarchi et al. | |
| 6,706,055 B2 * | 3/2004 | Douk et al. | 606/200 |
| 2002/0169472 A1 | 11/2002 | Douk et al. | |

FOREIGN PATENT DOCUMENTS

| | | |
|---|---|---|
| EP | 0689851 | 1/1996 |
| EP | 1344502 | 9/2003 |

* cited by examiner

*Primary Examiner*—Glenn K. Dawson
(74) *Attorney, Agent, or Firm*—James F. Crittenden

(57) ABSTRACT

A steerable guidewire apparatus for use during percutaneous catheter interventions such as angioplasty or stent deployment. A protection element comprising a filter or an occluder is mounted near the distal end of the steerable guidewire, which guides a therapeutic catheter. The guidewire comprises a hollow shaft movably disposed about a core wire. The shaft and core wire control separation of the ends of the protection element, causing transformation of the protection element from a deployed configuration to a collapsed configuration. Farther separation of the ends of the protection element, after it has been collapsed, causes deflection in a distal region of the apparatus.

6 Claims, 8 Drawing Sheets

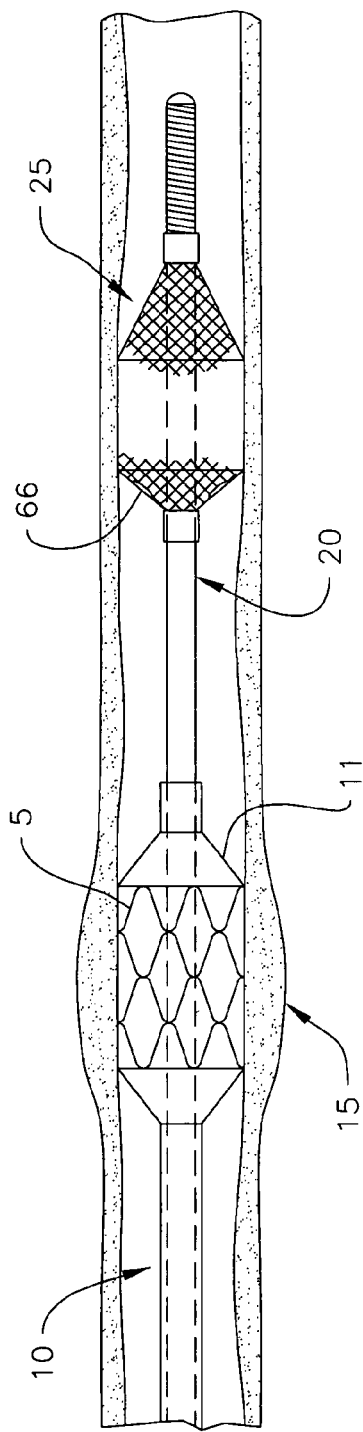
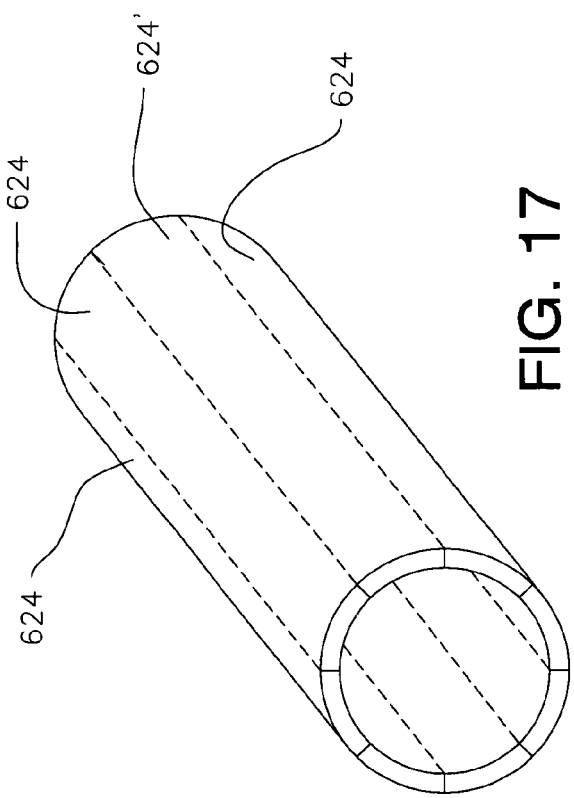

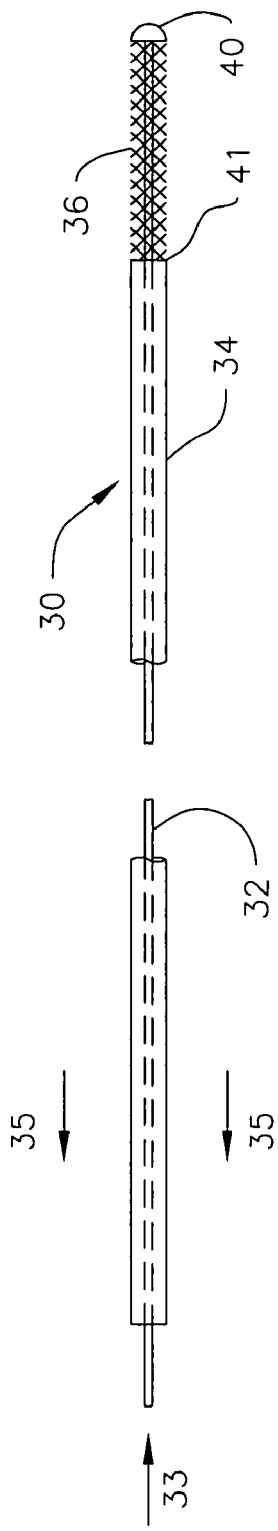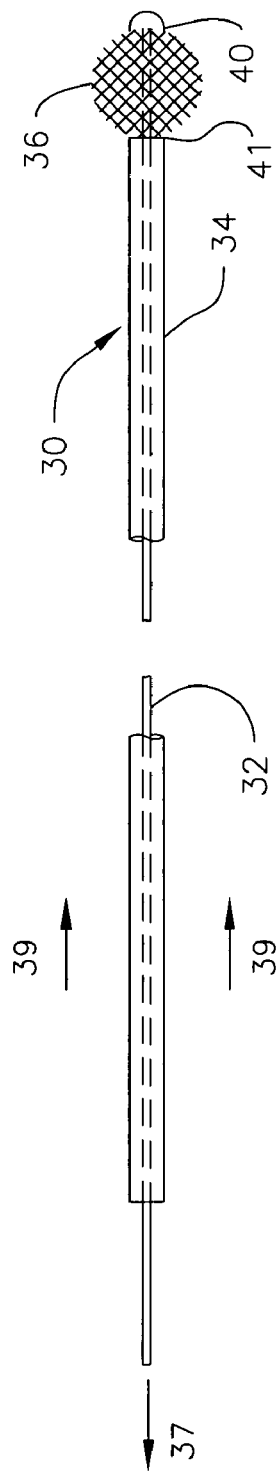
FIG. 3 (PRIOR ART)
FIG. 4 (PRIOR ART)

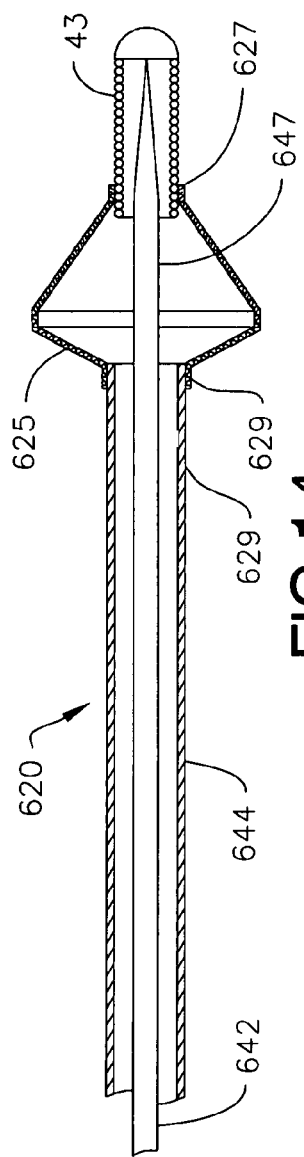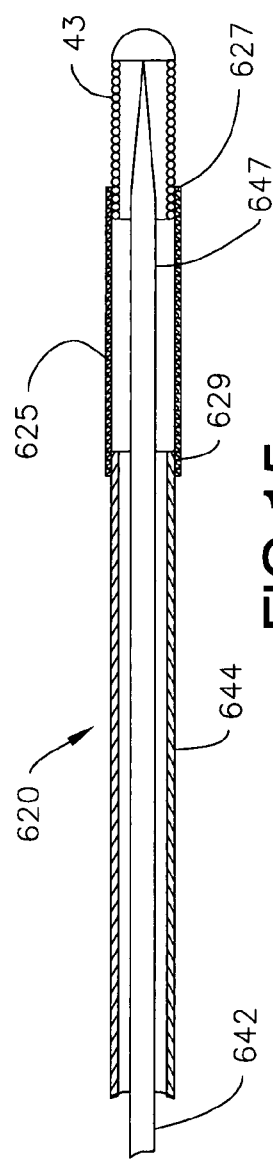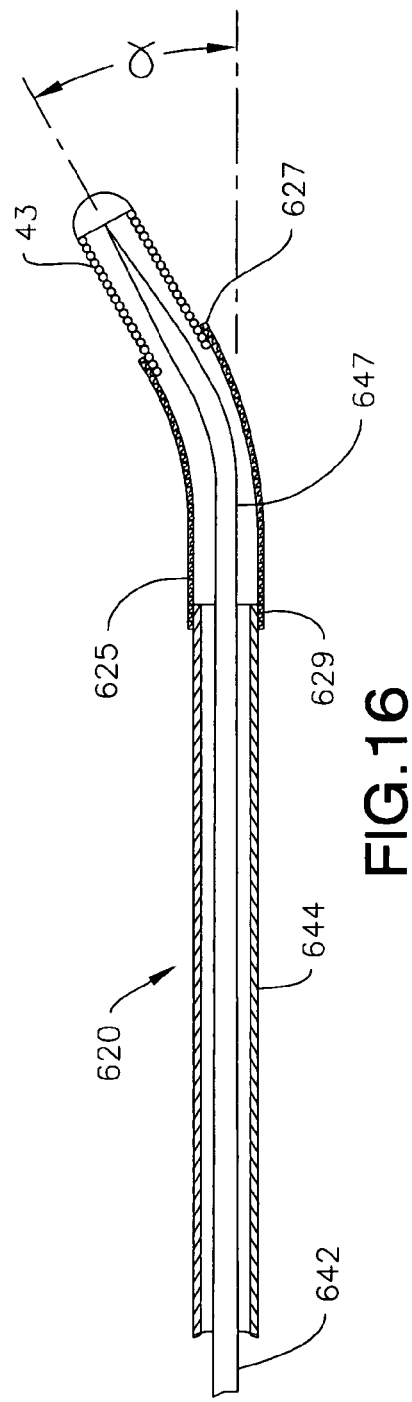

STEERABLE DISTAL PROTECTION GUIDEWIRE AND METHODS OF USE

FIELD OF THE INVENTION

The present invention relates generally to intraluminal devices for capturing particulate in the vessels of a patient. More particularly, the invention relates to a filter or an occluder for capturing emboli in a blood vessel during an interventional vascular procedure, then removing the captured emboli from the patient after completion of the procedure. Furthermore, the invention concerns a filter or an occluder mounted on a guidewire that can also be used to direct an interventional catheter to a treatment site within a patient.

BACKGROUND OF THE INVENTION

A variety of treatments exists for dilating or removing atherosclerotic plaque in blood vessels. The use of an angioplasty balloon catheter is common in the art as a minimally invasive treatment to enlarge a stenotic or diseased blood vessel. When applied to the arteries of the heart, this treatment is known as percutaneous transluminal coronary angioplasty, or PTCA. To provide radial support to the treated vessel in order to prolong the positive effects of PTCA, a stent may be implanted in conjunction with the procedure.

Thrombectomy is a minimally invasive technique for removal of an entire thrombus or a sufficient portion of the thrombus to enlarge the stenotic or diseased blood vessel and may be accomplished instead of a PTCA procedure. Atherectomy is another well-known minimally invasive procedure that mechanically cuts or abrades a stenosis within the diseased portion of the vessel. Alternatively, ablation therapies use laser or RF signals to superheat or vaporize a thrombus within the vessel. Emboli loosened during such procedures may be removed from the patient through the catheter.

During each of these procedures, there is a risk that emboli dislodged by the procedure will migrate through the circulatory system and cause ischaemic events, such as infarction or stroke. Thus, practitioners have approached prevention of escaped emboli through use of occlusion devices, filters, lysing, and aspiration techniques. For example, it is known to remove the embolic material by suction through an aspiration lumen in the treatment catheter or by capturing emboli in a filter or occlusion device positioned distal of the treatment area.

SUMMARY OF THE INVENTION

The guidewire apparatus of the invention includes a protection element comprising a filter or an occluder mounted near the distal end of a steerable guidewire, which guides a therapeutic catheter. The guidewire apparatus comprises a hollow shaft movably disposed about a core wire. The shaft and core wire control relative displacement of the ends of the protection element, causing transformation of the protection element between a deployed configuration and a collapsed configuration. After the collapsed configuration has been reached, applying further axial tension or distention to the protection element creates curvature therein, the curvature inducing a corresponding angular deflection in the underlying distal region of the core wire. The deflected distal region helps in steering the guidewire through tortuous vessels.

BRIEF DESCRIPTION OF THE DRAWINGS

Features, aspects and advantages of the present invention will become better understood with reference to the following description, appended claims, and accompanying drawings where:

FIG. 1 is an illustration of a filter system in accordance with the invention deployed within a blood vessel.

FIG. 3 is an illustration of a prior art expandable mesh device, shown with the mesh in a collapsed configuration;

FIG. 4 is an illustration of a prior art expandable mesh device, shown with the mesh in a deployed configuration;

FIG. 14 illustrates a tubular protection element in a deployed configuration in accordance with the invention;

FIG. 15 illustrates a tubular protection element in a collapsed configuration in accordance with the invention;

FIG. 16 illustrates a tubular protection element in a collapsed and deflected configuration in accordance with the invention; and FIG. 17 is an isometric view of a tubular protection element in accordance with the invention.

The drawings are not to scale.

DETAILED DESCRIPTION OF THE INVENTION

Figure 2:
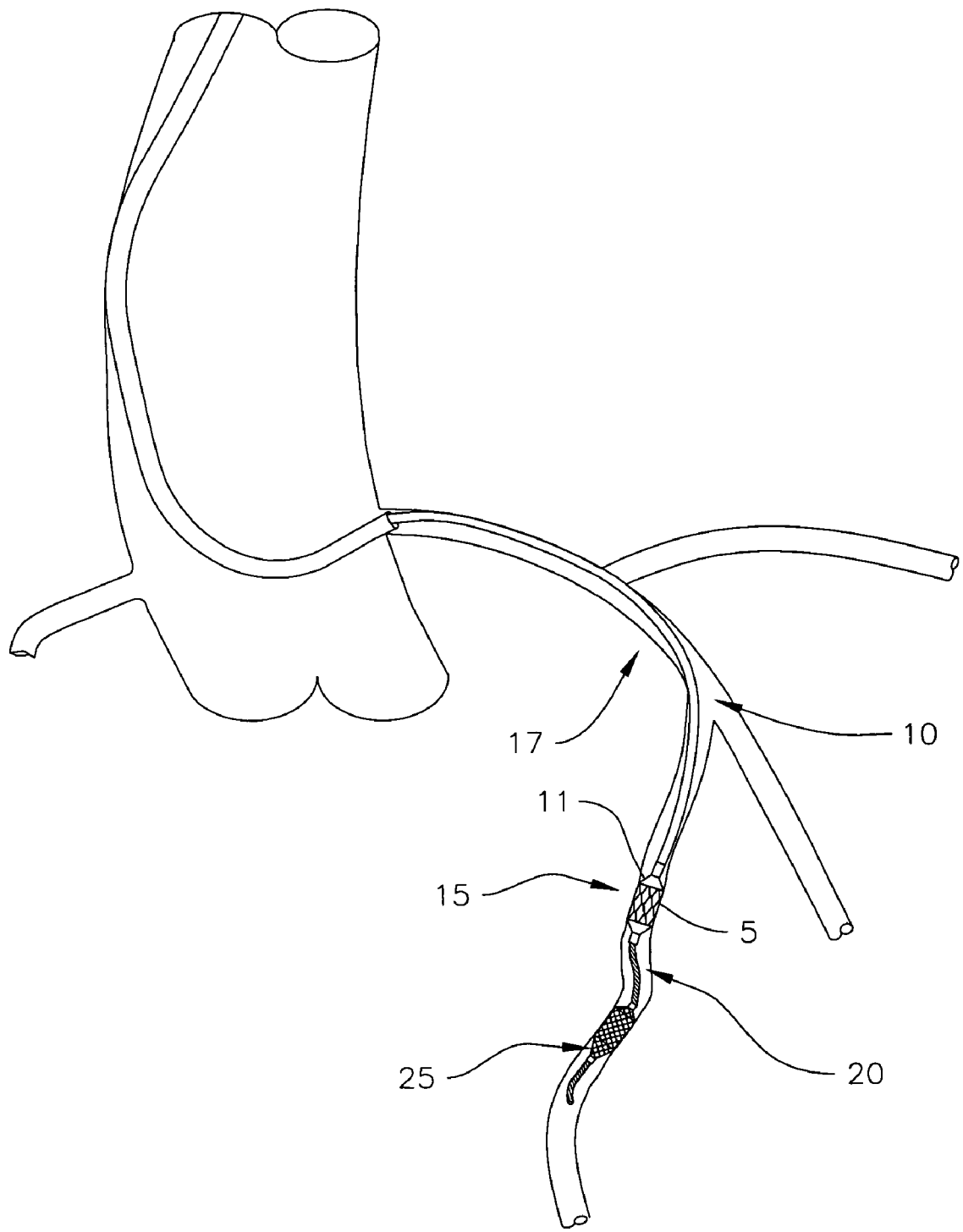
FIG. 2 is an illustration of a filter system in accordance with the invention deployed within a portion of the coronary arterial anatomy.

The present invention is a guidewire apparatus for use in minimally invasive procedures. While the following description of the invention relates to vascular interventions, it is to be understood that the invention is applicable to other procedures where the practitioner desires to capture embolic material that may be dislodged during the procedure. Intravascular procedures such as PTCA or stent deployment are often preferable to more invasive surgical techniques in the treatment of vascular narrowings, called stenoses or lesions. With reference to FIGS. 1 and 2, deployment of balloon expandable stent 5 is accomplished by threading catheter 10 through the vascular system of the patient until stent 5 is located within a stenosis at predetermined treatment site 15. Once positioned, balloon 11 of catheter 10 is inflated to expand stent 5 against the vascular wall to maintain the opening. Stent deployment can be performed following treatments such as angioplasty, or during initial balloon dilation of the treatment site, which is referred to as primary stenting.

Catheter 10 is typically guided to treatment site 15 by a guidewire. In cases where the target stenosis is located in tortuous, branching vessels that are remote from the vascular access point, such as coronary arteries 17 shown in FIG. 2, a steerable guidewire is commonly used. According to the present invention, a guidewire apparatus generally guides catheter 10 to treatment site 15 and includes a distally disposed protection element to collect embolic debris that may be generated during the procedure. Steerability of the guidewire apparatus is enhanced by the incorporation of a deflectable distal region. Thus, the clinician may deflect and/or rotate the distal region of the guidewire to enter selected branches or traverse particularly tortuous areas of the patient's vasculature. Various embodiments of the invention will be described as either filter guidewires or occluder guidewires. However, it is to be understood that filters and occluders are interchangeable types of protection elements among the inventive structures disclosed. The invention is directed to embolic protection elements wherein relative movement of the ends of the protection element cause transformation of the element between a collapsed configuration and an expanded, or deployed configuration. Such transformation may be impelled by external mechanical means or by self-shaping (self-expanding) memory within the protection element itself. Such mechanical memory can be imparted to the metal comprising the element by thermal treatment to achieve a spring temper in stainless steel, for example, or to set a shape memory in a susceptible metal alloy such as a nickel-titanium (nitinol) alloy.

Filter guidewires in accordance with the invention include distally disposed filter 25, which may comprise a tube formed by braided filaments that define pores and have at least one proximally-facing inlet opening 66 that is substantially larger than the pores. Alternative types of filters may be used in filter 25, such as filter assemblies that include a porous mesh mounted to expandable struts. Optionally, adding radiopaque markers (not shown) to filter ends 27, 29, can aid in fluoroscopic observation of filter 25 during manipulation thereof. Alternatively, to enhance visualization of braided filter 25 under fluoroscopy, at least one of the filaments may be a wire having enhanced radiopacity compared to conventional non-radiopaque wires suitable for braiding filter 25. At least the majority of braiding wires forming filter 25 should be capable of being heat set into the desired filter shape, and such wires should also have sufficient elastic properties to provide the desired self-expanding features. Stainless steel and nitinol monofilaments are suitable for braiding filter 25. A braiding wire having enhanced radiopacity may be made of, or coated with, a radiopaque metal such as gold, platinum, tungsten, alloys thereof, or other biocompatible metals that, compared with stainless steel or nitinol, have a relatively high X-ray attenuation coefficient. One or more filaments having enhanced radiopacity may be inter-woven with non-radiopaque wires, or all wires comprising filter 25 may have the same enhanced radiopacity.

In accordance with the invention, maintaining filter 25 in a collapsed configuration during introduction and withdrawal of filter guidewire 20 does not require a control sheath that slidingly envelops filter 25. Thus, this type of device is sometimes termed "sheathless." Known types of sheathless vascular filter devices are operated by a push-pull mechanism that is also typical of other expandable braid devices, as shown in FIGS. 3 and 4. Prior art expandable mesh device 30 includes core wire 32 and hollow shaft 34 movably disposed there about. Tubular mesh or braid 36 surrounds core wire 32 and has a braid distal end fixed to core wire distal end 40 and a braid proximal end fixed to shaft distal end 41. To expand braid 36, core wire 32 is pulled and shaft 34 is pushed, as shown by arrows 37 and 39 respectively in FIG. 4. The relative displacement of core wire 32 and shaft 34 moves the ends of braid 36 towards each other, forcing the middle region of braid 36 to expand. To collapse braid 36, core wire 32 is pushed and shaft 34 is pulled, as shown by arrows 33 and 35 respectively in FIG. 3. This reverse manipulation draws the ends of braid 36 apart, pulling the middle region of braid 36 radially inward toward core wire 32.

Figure 5:
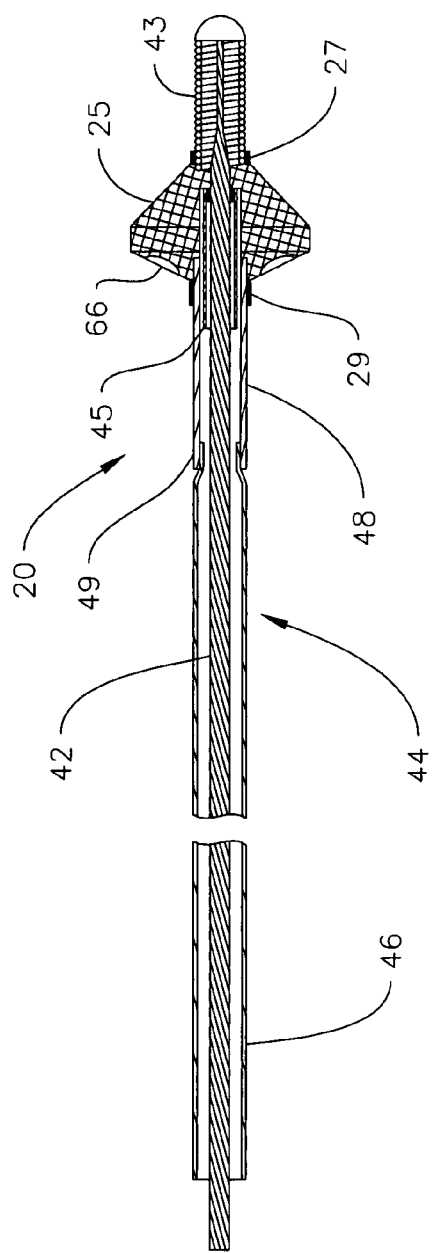
FIG. 5 is a longitudinal sectional view of a first guidewire embodiment in accordance with the invention.

Referring now to FIG. 5, in a first embodiment of the invention, filter guidewire 20 includes core wire 42 and flexible tubular tip member 43, such as a coil spring, fixed around the distal end of core wire 42. Thin wires made from stainless steel and/or one of various alloys of platinum are commonly used to make coil springs for such use in guidewires. Core wire 42 can be made from shape memory metal such as nitinol, or a stainless steel wire, and typically is tapered at its distal end. For treating small caliber vessels such as coronary arteries, core wire 42 may measure about 0.15 mm (0.006 inch) in diameter.

In filter guidewire 20, hollow shaft 44 is movably disposed around core wire 42, and includes relatively stiff proximal portion 46 and relatively flexible distal portion 48. Proximal portion 46 may be made from thin walled stainless steel tubing, usually referred to as hypo tubing, although other metals, such as nitinol, can be used. Various metals or polymers can be used to make relatively flexible distal portion 48. One appropriate material for this element is thermoset polyimide (PI) tubing, available from sources such as HV Technologies, Inc., Trenton, Ga., U.S.A. The length of distal portion 48 may be selected as appropriate for the intended use of the filter guidewire. In one example, portion 48 may be designed and intended to be flexible enough to negotiate tortuous coronary arteries, in which case the length of portion 48 may be 15-35 cm (5.9-13.8 inches), or at least approximately 25 cm (9.8 inches). In comparison to treatment of coronary vessels, adaptations of the invention for treatment of renal arteries may require a relatively shorter flexible portion 48, and neurovascular versions intended for approaching vessels in the head and neck may require a relatively longer flexible portion 48.

When filter guidewire 20 is designed for use in small vessels, shaft 44 may have an outer diameter of about 0.36 mm (0.014 inch). The general uniformity of the outer diameter may be maintained by connecting proximal portion 46 and distal portion 48 with lap joint 49. Lap joint 49, and all other adhesive joints in the invention, may use any suitable biocompatible adhesive such as ultraviolet (UV) light curable adhesives, thermally curable adhesives or so-called "instant" cyanoacrylate adhesives from Dymax Corporation, Torrington, Conn., U.S.A. or Loctite Corporation, Rocky Hill, Conn., U.S.A. Lap joint 49 can be formed by any conventional method such as reducing the wall thickness of proximal portion 46 in the region of joint 49, or by forming a step-down in diameter at this location with negligible change in wall thickness, as by swaging.

Figure 12:
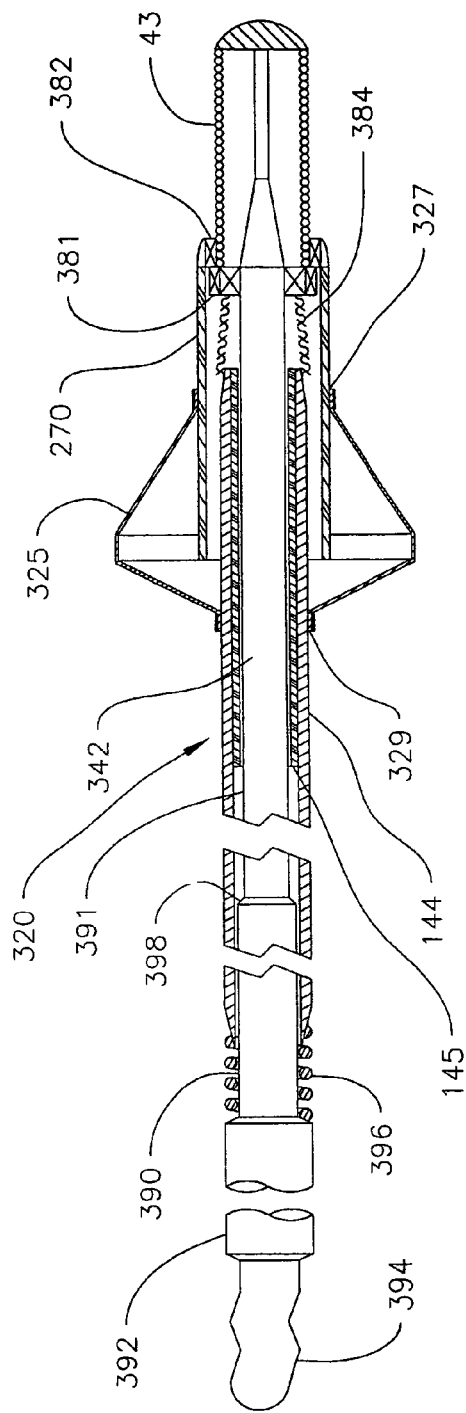
FIG. 12 is a partially sectioned longitudinal view of a fourth guidewire embodiment in accordance with the invention.
Figure 13:
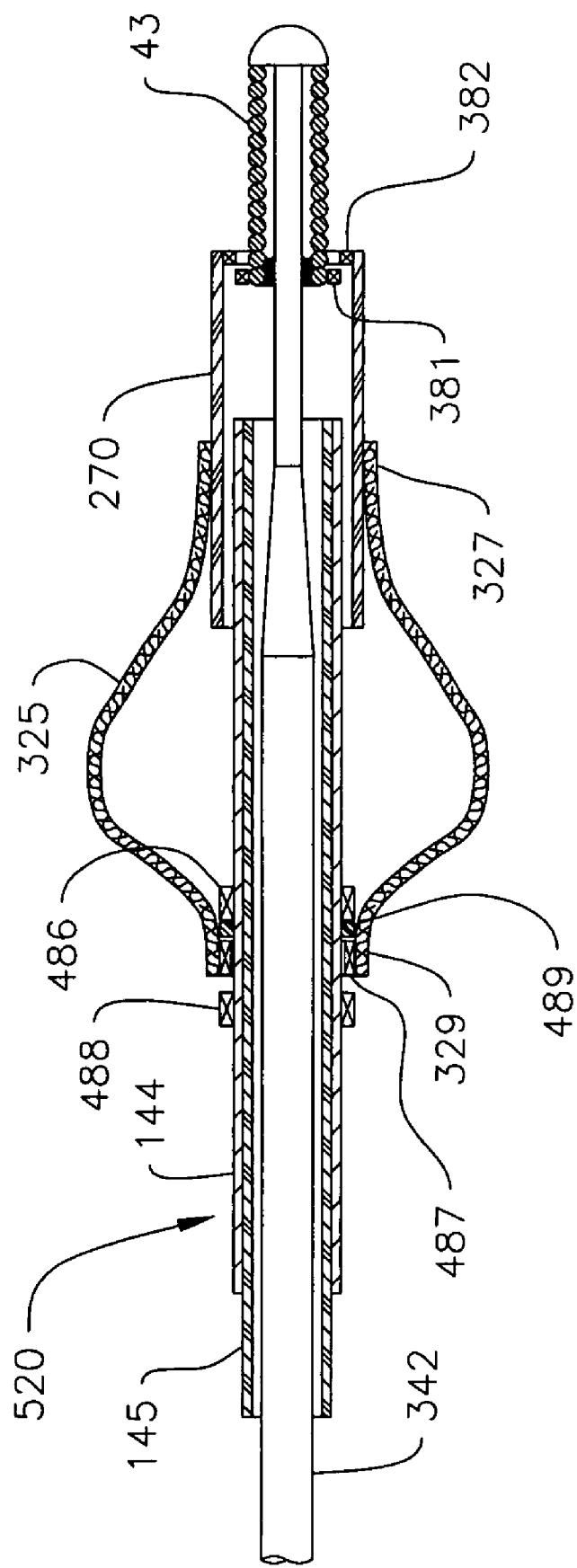
FIG. 13 is a partially sectioned longitudinal view of a fifth guidewire embodiment in accordance with the invention.

Expandable tubular filter 25 is positioned generally concentrically with core wire 42, and is sized such that when it is fully deployed, as shown in FIGS. 1 and 2, the outer perimeter of filter 25 will contact the inner surface of the vessel wall. The surface contact is maintained around the entire vessel lumen to prevent any emboli from slipping past filter 25. Adhesive may be used to secure filter distal end 27 to tip member 43, and to secure filter proximal end 29 near the distal end of shaft 44. As shown in FIGS. 12 and 13, radiopaque marker bands, such as platinum rings, can be incorporated into the adhesive joints securing filter ends 27, 29 respectively to tip member 43 and shaft 44. Filter 25 is deployed by advancing, or pushing shaft 44 relative to core wire 42 such that filter distal and proximal ends 27, 29 are drawn toward each other, forcing the middle, or central section of filter 25 to expand radially. Filter 25 is collapsed by withdrawing, or pulling shaft 44 relative to core wire 42 such that filter distal and proximal ends 27, 29 are drawn apart from each other, forcing the middle, or central section of filter 25 to contract radially.

Transition sleeve 45 is fixed about core wire 42 and is slidably located within the distal end of flexible distal portion 48 of hollow shaft 44. Transition sleeve 45 may be made of polyimide tubing similar to that used in distal portion 48 and extends distally there from. By partially filling the annular space between core wire 42 and shaft 44, and by contributing additional stiffness over its length, sleeve 45 supports core wire 42 and provides a gradual transition in overall stiffness of filter guidewire 20 adjacent the distal end of shaft 44. Transition sleeve 45 is fixed to core wire 42 with a suitable adhesive, such that relative displacement between shaft 44 and core wire 42 causes corresponding relative displacement between shaft 44 and sleeve 45. The length and mounting position of sleeve 45 are selected such that sleeve 45 spans the distal end of shaft 44 regardless of the configuration of filter 25 and the corresponding position of shaft 44 relative to core wire 42. When constructed as described above, filter guidewire 20 provides the functions of a temporary filter combined with the performance of a steerable guidewire.

Figure 6:
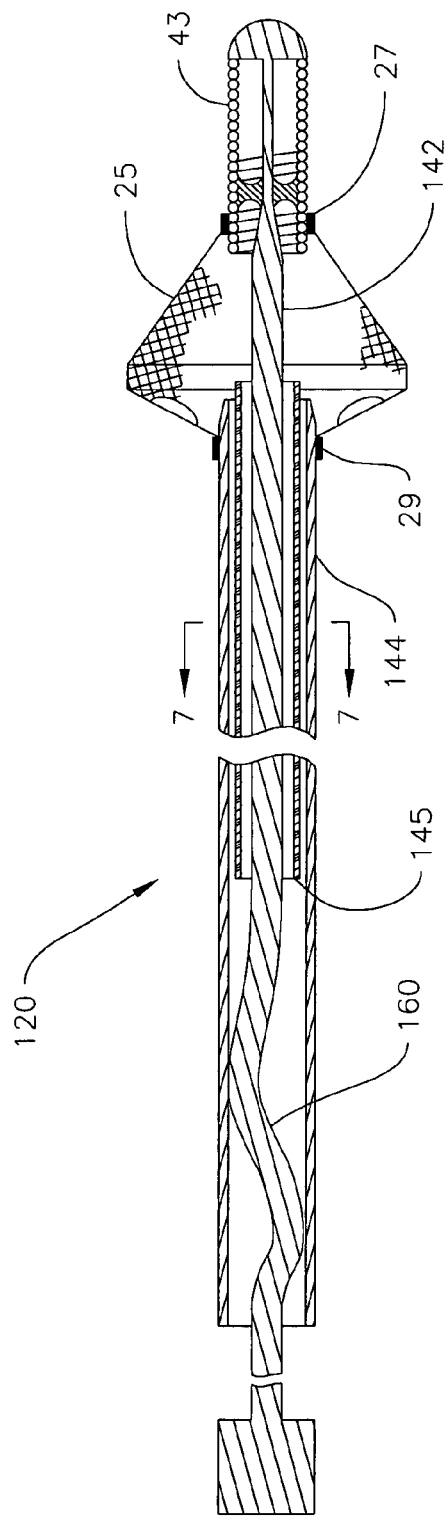
FIG. 6 is a longitudinal sectional view of a second guidewire embodiment in accordance with the invention.

FIG. 6 depicts a second embodiment of the invention in which filter guidewire 120 incorporates a number of elements similar to the elements that make up filter guidewire 20. Such similar elements will be identified with the same reference numerals throughout the description of the invention. Filter guidewire 120 includes core wire 142 and flexible tubular tip member 43 fixed around the distal end of core wire 142, similar to the arrangement of guidewire 20, above. Hollow shaft 144 is movably disposed around core wire 142 and is comparable, throughout its length, to relatively stiff proximal portion 46 of filter guidewire 20. Filter 25 is positioned generally concentrically with core wire 142. Filter distal end 27 is fixedly coupled to tip member 43, and filter proximal end 29 is fixedly coupled near the distal end of shaft 144.

Optionally, a portion of core wire 142 within the proximal end of shaft 144 has one or more bends 160 formed therein. The amplitude or maximal transverse dimension of bends 160 is selected such that the bent portion of core wire 142 fits, with interference, within shaft 144. The interference fit provides sufficient friction to hold core wire 142 and shaft 144 in desired axial positions relative to each other, thereby controlling the shape of filter 25, as described above with respect to filter guidewire 20.

In filter guidewire 120, liner 145 is interfitted as a low-friction axial bearing in the annular space between core wire 142 and shaft 144. With respect to the three coaxially arranged elements, the selected dimensions and the stack-up of dimensional tolerances will determine how liner 145 functions during the push-pull operation of core wire 142 within shaft 144.

Figures 7, 8:
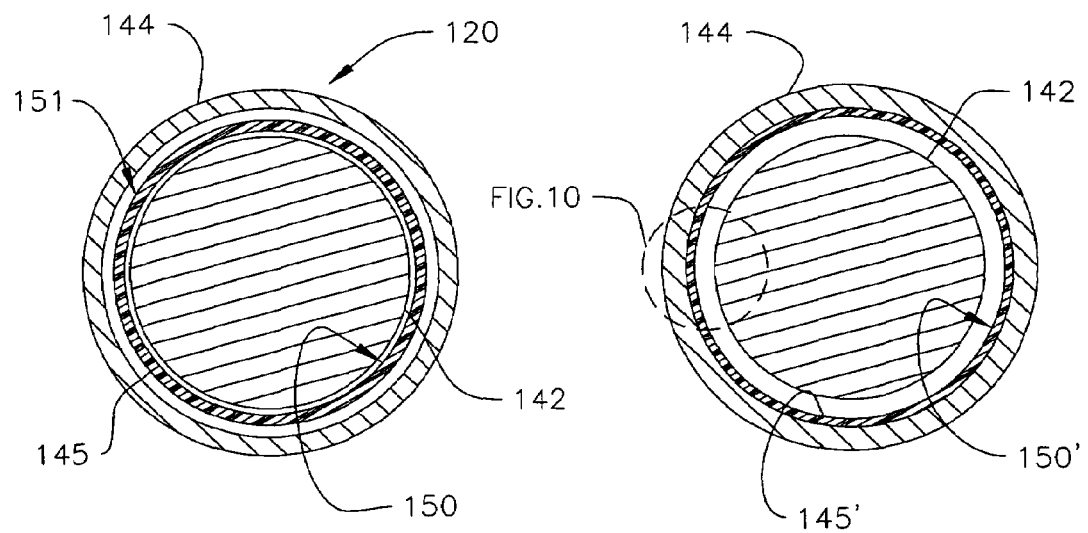
FIG. 7 is a cross-sectional view of the second guidewire embodiment taken along the lines 7 B 7 of FIG. 6.
FIG. 8 is a modified form of the cross-sectional view shown in FIG. 7.

For example, FIG. 7 depicts a cross-section of filter guidewire 120 in which there is radial clearance between liner inner surface 150 and core wire 142, and there also is radial clearance between liner outer surface 151 and the inner wall of shaft 144. In this arrangement, liner 145 is radially free-floating in the annular space between core wire 142 and shaft 144. The length of liner 145 is selected such that it also "floats" axially along core wire 142. The axial movement of liner 145 along core wire 142 is limited proximally by a stop formed at the engagement of bends 160 with the inner wall of shaft 144. Tip member 43 limits the axial distal movement of liner 145 along core wire 142. The radial and axial flotation of liner 145 in filter guidewire 120 provides an axial bearing wherein the components with the lesser relative coefficient of friction can slide against each other. For example, if the coefficient of friction between liner inner surface 150 and core wire 142 is less than the coefficient of friction between liner outer surface 151 and the inner wall of shaft 144, then liner 145 will remain longitudinally fixed within shaft 144, and push-pull action will cause core wire 142 to slide within liner 145. Conversely, if the coefficient of friction between liner inner surface 150 and core wire 142 is greater than the coefficient of friction between liner outer surface 151 and the inner wall of shaft 144, then liner 145 will remain longitudinally fixed about core wire 142, and push-pull action will cause shaft 144 to slide over liner 145. The relative coefficients of friction for the movable components of the guidewire assembly may be designed-in by selection of materials and/or coatings, as will be described below. Alternatively, the degree of sliding friction may result from unplanned events, such as the formation of thrombus on one or more component surfaces or embolic debris entering the annular space(s) there between.

Figures 9, 10:
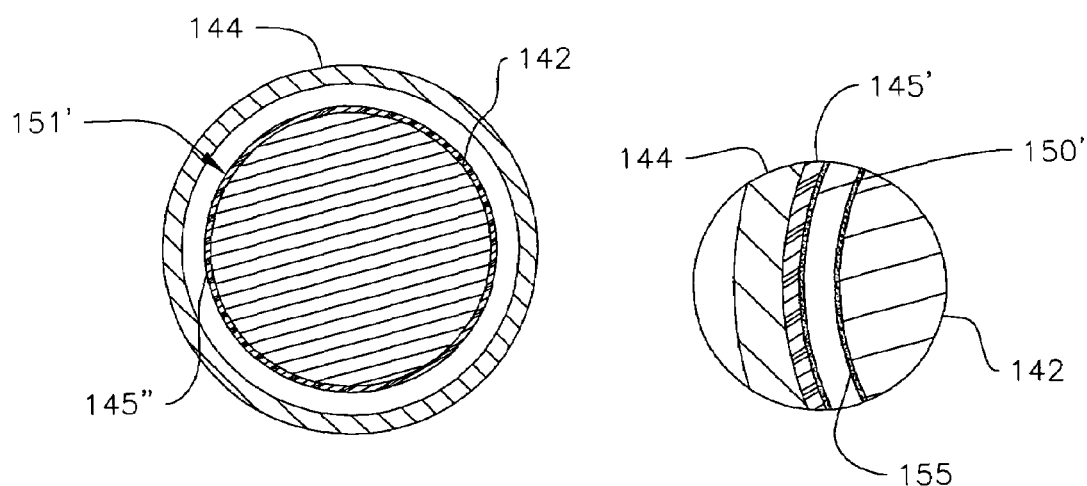
FIG. 9 is another modified form of the cross-sectional view shown in FIG. 7.
FIG. 10 is an enlarged supplementary view of a portion of FIG. 8, which has been modified to illustrate alternative embodiments of the invention.

FIG. 8 depicts a modified form of the cross-sectional view shown in FIG. 7 in which liner 145' is fitted against the inner wall of shaft 144, leaving radial clearance only between liner inner surface 150' and core wire 142. FIG. 9 depicts another modified form of the cross-sectional view shown in FIG. 7 in which liner 145" is fitted against core wire 142, leaving radial clearance only between liner outer surface 151' and the inner wall of shaft 144.

When filter guidewire 120 is designed for use in small vessels, shaft 144 may have an outer diameter of about 0.36 mm (0.014 inch), and core wire 142 may measure about 0.15 mm (0.006 inch) in diameter. Shaft 144, which can be made from hypo tubing, may have an inside diameter of about 0.23 mm (0.009 inch). For liner 145 to "float" in an annular space between core wire 142 and shaft 144 with such dimensions, liner outer surface 151 may measure about 0.22 mm (0.0088 inch) in diameter and liner inner surface 150 may measure about 0.18 mm (0.0069 inch) in diameter. Liner 145' does not require clearance around its outside diameter, because it is fitted against the inner wall of shaft 144. As compared to liner 145, liner 145' may have a greater wall thickness, and liner inner surface 150' may have a similar inner diameter of about 0.18 mm (0.0069 inch). Liner 145" does not require inside clearance because it is fitted against core wire 142. As compared to liner 145, liner 145" may also have greater wall thickness, and liner outer surface 151' may have a similar outer diameter of about 0.22 mm (0.0088 inch).

Liners 145, 145' and 145" may be formed of polymers selected to provide low coefficients of friction on their sliding surfaces. Typical of such polymers are polytetrafluoroethylene (PTFE), fluorinated ethylene-propylene (FEP), high-density polyethylene (HDPE), and various polyamides (nylons). Alternatively, liners 145, 145' and 145" may be formed of a material selected for physical properties other than a low coefficient of friction, i.e. stiffness or ability to be formed with tight dimensional tolerances. For such materials, a slippery coating, such as silicone, may be applied to the sliding surface(s) in order to achieve the desired low-friction axial bearing properties.

Thermoset polyimide (PI) is an example of a liner material that may be selected for properties other than its coefficient of friction. PI tubing is noted for its ability to be formed with tight dimensional tolerances because it is typically formed by building up several layers of cured PI coating around a solid glass core, which is removed by chemical etching. One method of creating a slippery surface on PI tubing is to add a fluoropolymer filler, such as PTFE or FEP, to the PI coating to form one or more low-friction layers at the desired surface(s). Such polyimide/fluoropolymer composite tubing is available from MicroLumen, Inc., Tampa, Fla., U.S.A. FIG. 10 illustrates a modified form of the invention wherein the inner surface of liner 145' comprises lubricious coating 150'. Also shown in FIG. 10 is slippery coating 155, which may be applied to core wire 142 in conjunction with, or instead of, a slippery inner surface of liners 145 or 145'. Coating 155 may comprise a thin film of, for example, silicone or a fluoropolymer.

Another example of a liner material that may be selected for properties other than its coefficient of friction is a block copolymer thermoplastic such as polyethylene block amide (PEBA). Although a slippery coating may be applied to this material, alternatively, plasma-aided surface polymerization may be used to reduce its coefficient of friction. Plasma-aided surface functionalization to achieve high lubricity is described in U.S. Pat. No. 4,693,799 (Yanagihara et al.), and plasma surface modification is available from AST Products, Inc., Billerica, Mass., U.S.A. Plasma treated PEBA may be substituted for PTFE in liners to make use of improved physical properties, including the ability to be plastically extruded.

Figure 11:
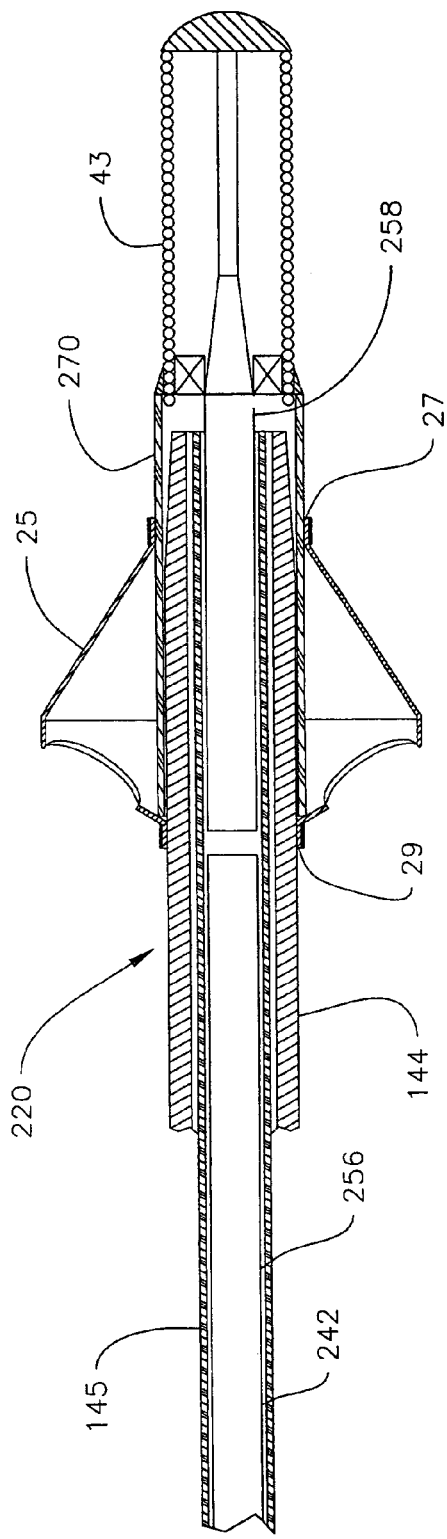
FIG. 11 is a partially sectioned longitudinal view of a third guidewire embodiment in accordance with the invention.

FIG. 11 depicts a third embodiment of the invention in which filter guidewire 220 incorporates several elements that are similar to the components of filter guidewires 20 and 120. Core wire 242 is disposed within liner 145, which is disposed within hollow shaft 144. Core wire 242 is comprised of proximal section 256 and separate distal section 258, which extends distally from shaft 144. Sliding clearance(s) may be formed between different elongate movable components, as described above and as shown in FIGS. 7, 8 and 9. If liner 145 is fitted against core wire 242, as shown in FIG. 9, then liner 145 will comprise separate proximal and distal sections (not shown) corresponding to core wire proximal section 256 and core wire distal section 258. Flexible tubular tip member 43 is fixed around the distal end of core wire distal section 258. Transition sleeve 270 is slidably disposed about a distal portion of hollow shaft 144 and extends distally there from to a fixed coupling location on tip member 43. Filter 25 is self-expanding and is positioned generally concentrically with the distal portion of shaft 144. Filter distal end 27 is fixedly coupled to transition sleeve 270, and filter proximal end 29 is fixedly coupled to shaft 144 adjacent the distal portion thereof.

Prior to negotiating vascular anatomy with filter guidewire 220, filter 25 may be collapsed by advancing core wire proximal section 256 within shaft 144 and liner 145 until the distal end of proximal section 256 abuts the proximal end of distal section 258, forming continuous core wire 242. Continued advancement of core wire 242 through shaft 144 and liner 145 will displace tip member 43 distally away from shaft 144. The axial translation of tip member 43 will draw sleeve 270 distally along, but not off, the distal portion of hollow shaft 144. The relative longitudinal movement of sleeve 270 with respect to shaft 144 causes filter distal end 27 to move away from filter proximal end 29, transforming filter 25 from its expanded configuration to its collapsed configuration. Optionally, filter guidewire 220 may include bends 160 (not shown) in core wire proximal section 256 to provide frictional engagement between core wire 242 and the proximal end of shaft 144. As described above regarding filter guidewire 120, the optional friction mechanism thus created can hold core wire 242 in a selected axial position within shaft 144, thereby retaining filter 25 in the collapsed configuration.

Withdrawing core wire proximal section 256 proximally through shaft 144 and liner 145 allows filter 25 to transform itself towards the expanded configuration by drawing filter ends 27, 29 closer together. The self-transformation of filter 25 towards the expanded configuration causes simultaneous proximal movement of sleeve 270, tip member 43 and core wire distal section 258 relative to shaft 144. The self-expansion of filter 25 stops when a) filter 25 reaches its pre-formed expanded configuration, or b) filter 25 encounters a radial constraint, such as apposition with a vessel wall in a patient, or c) filter 25 encounters an axial constraint, such as the proximal end of sleeve 270 contacting filter proximal end 29, as depicted in FIG. 12. After self-expansion of filter 25 has stopped, any further withdrawal of core wire proximal section 256 will cause it to separate from core wire distal section 258, thereby allowing core wire distal section 258, tip member 43, and sleeve 270 to move freely with respect to the distal end of hollow shaft 144. In this configuration, core wire proximal section 256 will not interfere with self-expansion or self-adjustment of filter 25 in its apposition with the vessel wall.

Transition sleeve 270 may be made of polyimide tubing and may be fixed to tip member 43 and to filter distal end 27 with a suitable adhesive. The length and mounting position of sleeve 270 are selected such that sleeve 270 always surrounds the distal end of shaft 144, regardless of the configuration and length of filter 25. Sleeve 270 can support core wire 242 across the longitudinal gap between the distal end of shaft 144 and the proximal end of tip member 43. By contributing additional stiffness over its length, sleeve 270 also provides a transition in overall stiffness of filter guidewire 220 adjacent the distal end of shaft 144.

FIG. 12 depicts a fourth embodiment of the invention in which occluder guidewire 320 incorporates several elements that are similar to the components of filter guidewires 20, 120, and 220. As distinguished from filter guidewire embodiments of the invention, occluder guidewires are typically used to temporarily obstruct fluid flow through the vessel being treated. Any embolic debris trapped upstream of the occluder element may be aspirated using a separate catheter, with or without irrigation of the area. Core wire 342 is disposed within liner 145, which is disposed within hollow shaft 144. Alternatively, liners 145' or 145" may be substituted for liner 145 such that different sliding clearance (s) may be formed between different elongate movable components, as described above and as shown in FIGS. 7, 8 and 9. Flexible tubular tip member 43 is fixed around the distal end of core 342. Transition sleeve 270 is slidably disposed about a distal portion of hollow shaft 144 and extends distally there from to a sliding coupling located on tip member 43. Proximal stop 381 protrudes radially outward from the proximal end of tip member 43, and distal stop 382 protrudes radially inward from the distal end of transition sleeve 270. Stops 381, 382 interact to prevent the distal end of transition sleeve 270 from sliding proximally off tip member 43. Proximal stop 381 may comprise a portion of tip member 43, such as one or more enlarged turns at the proximal end of a coil spring. Alternatively, proximal stop 381 may be created with metal or plastic elements, such as solder or polyimide bands. Distal stop 382 may comprise a portion of transition sleeve 270, such as a rim or neck of reduced diameter formed at the distal end thereof. Alternatively, distal stop 382 may be created with metal or plastic elements, such as polyimide rings or bands.

Occluder 325 is self-expanding and is positioned generally concentrically with the distal portion of shaft 144. Similar to filter 25, occluder 325 may comprise a tubular braid, which in this embodiment is coated with an elastic material to render it non-porous. Alternatively, occluder 325 may include self-expanding struts (not shown) that support a non-porous elastic membrane, as known to those of ordinary skill in the art. A non-porous coating or membrane may be made from a variety of elastic materials, such as silicone rubber or a thermoplastic elastomer (TPE). Occluder distal end 327 is fixedly coupled to transition sleeve 270, and occluder proximal end 329 is fixedly coupled to shaft 144 proximally adjacent the distal portion thereof.

In occluder guidewire 320, occluder 325 may be collapsed by advancing core wire 342 through shaft 144 and liner 145, causing tip member 43 to translate within transition sleeve 270 until proximal stop 381 engages distal stop 382, as shown in FIG. 12. Continued advancement of core wire 342 through shaft 144 and liner 145 will displace tip member 43 distally from shaft 144, drawing sleeve 270 along, but not off, the distal portion of hollow shaft 144. The relative longitudinal movement of sleeve 270 with respect to shaft 144 causes occluder distal end 327 to move away from occluder proximal end 329, which transforms occluder 325 from its expanded configuration to its collapsed configuration. Reversing the above manipulation, i.e. drawing core wire 342 proximally through shaft 144 and liner 145, permits occluder 325 to expand itself. Self-expansion of occluder 325 will stop when one of several conditions is met, as described above with respect to self-expanding filter 25 of filter guidewire 220. Thereafter, continued withdrawal of core wire 342 will draw tip member 43 proximally within transition sleeve 270, creating axial separation (not shown) between stops 381, 382, thereby allowing the distal end of transition sleeve 270, with distal stop 382, to slide freely along tip member 43. In this configuration, core wire 342 and tip member 43 will not interfere with self-expansion or self-adjustment of occluder 325 in its apposition with the vessel wall.

FIG. 12 illustrates the portion of core wire 342 within hollow shaft 144 having a first proximal segment 390, which also extends proximally from hollow shaft 144. First proximal segment 390 is sized to fit slidingly within hollow shaft 144, but without sufficient radial clearance for liners 145, 145' or 145". First proximal segment 390 may comprise a major length of core wire 342, such that relatively short core wire distal segment 391 is dimensioned to receive liners 145, 145' or 145". For example, if occluder guidewire 320 is designed for use in coronary arteries, then the overall length of core wire 342 may be about 175 cm, and the length of core wire distal segment 391 may be about 15 to 25 cm. Alternatively, first proximal segment 390 may have a relatively short length such that core wire distal segment 391 and surrounding liners 145, 145' or 145" extend through a major length of hollow shaft 144.

The transition in diameter between core wire distal segment 391 and first proximal segment 390 may occur as step 398, which can limit the proximal slippage of free-floating liner 145 along core wire 342. Optionally, occluder guidewire 320 may exclude any liner while still incorporating stepped diameter core wire 342 shown in FIG. 12. In such an arrangement, the annular space that would otherwise be occupied by a liner can provide enlarged clearance and accompanying reduced friction between core wire 342 and hollow shaft 144, especially when occluder guidewire 320 is curved through tortuous anatomy. Core wire 342 may also optionally include bends 160 (not shown) located distal to first proximal segment 390.

In order to steer a distal protection guidewire in accordance with the invention through tortuous vasculature, tip member 43 is typically bent or curved prior to insertion of the device. As in all steerable guidewires, the steerable distal protection guidewires of the invention transmit to tip member 43 substantially all of the rotation, or torque applied by the clinician to the proximal end of the device. It is most convenient for the physician to steer the device by grasping and rotating shaft 144, and having such rotation imparted to tip member 43, either directly or through the core wire. In distal protection guidewires of the instant invention, various design features reduce longitudinal friction between the hollow shaft and the core wire. These same friction-reducing features also reduce rotational friction between the hollow shaft and the core wire, which would otherwise be useful in transmitting rotation to steer the device. In filter guidewires 20, 120 and 220, torque is transmissible from shaft 144 to tip member 43 through the braided structure of filter 25. However, this path of torque transmission is generally effective only when filter 25 is in the collapsed configuration. In occluder guidewire 320, occluder distal end 327 is slidably connected to tip member 43 through transition sleeve 270 such that torque cannot be transmitted from shaft 144 to tip member 43 through occluder 325.

It is therefore advantageous, as shown in occluder guidewire 320, to include a torque-transmitting element, such as torque member 384. Torque member 384 can comprise metal or plastic filaments that form a hollow tube of counter wound spirals or a braid. To minimize bulk and stiffness, torque member 384 may include only a single filament in each of the clockwise and counter clockwise winding directions. The proximal end of torque member 384 is bonded to the distal end of shaft 144 and torque member 384 extends distally there from to surround core wire 342 over a relatively short distance. The distal end of torque member 384 is bonded to the proximal end of tip member 43 or to core wire 342 adjacent thereto. The braided, or spirally wound tubular structure of torque member 384 permits it to transmit rotation forces between shaft 144 and tip member 43, and to do so at any length required to accommodate longitudinal displacement of shaft 144 and tip member 43 during transformation of occluder element 325 between a collapsed configuration and an expanded configuration.

In occluder guidewire 320, second proximal segment 392 is located proximally of first proximal segment 390 and has an enlarged diameter approximating the outer diameter of shaft 144. Reinforcement coil 396 surrounds first proximal segment 390 between second proximal segment 392 and the proximal end of hollow shaft 144. Coil 396 has about the same outer diameter as shaft 144, and helps prevent kinking of the portion of first proximal segment 390 that extends from hollow shaft 144. Reinforcement coil 396 can vary in length to accommodate longitudinal displacement of shaft 144 and core wire 342 during transformation of occluder element 325 between a collapsed configuration and an expanded configuration.

Third proximal segment 394 is located proximally of second proximal segment 392 and is adapted for engagement to a guidewire extension (not shown), as is well known to those of ordinary skill in the art of guidewires. Examples of guidewire extensions usable with occluder guidewire 320 and other embodiments of the invention are shown in U.S. Pat. No. 4,827,941 (Taylor), U.S. Pat. No. 5,113,872 (Jahrmarkt et al.) and U.S. Pat. No. 5,133,364 (Palermo et al.).

FIG. 13 depicts a fifth embodiment of the invention in which occluder guidewire 520 incorporates several elements that are similar to the components of occluder guidewire 320. Elements, and their positions, that are common to occluder guidewires 320 and 520 are shaft 144, liner 145, transition sleeve 270, occluder 325, core wire 342, tip member 43, and stops 381, 382. Occluder guidewire 520 has slip ring 487 fixed within occluder proximal end 329. Slip ring 487 is rotatably mounted about hollow shaft 144 between distal and proximal check elements 486, 488 respectively.

In occluder guidewire 520, distal check element 486 protrudes radially outward from shaft 144 distal of occluder proximal end 329. When hollow shaft 144 is drawn proximally over core wire 342, distal check element 486 may contact occluder proximal end 329, to which it may transmit proximally directed force from shaft 144. Optionally, proximal check element 488 protrudes radially outward from shaft 144 proximal of occluder proximal end 329. When hollow shaft 144 is slid distally over core wire 342, proximal check element 488 may contact occluder proximal end 329, to which it may transmit distally directed force from shaft 144. Distal and proximal check elements 486, 488 may comprise rings, bands, coils, pins, adhesive dots, distortions in shaft 144, or any other cooperating features that can effectively check longitudinal movement of occluder proximal end 329 while permitting rotation thereof. Thus, proximal end 329 is rotatable about shaft 144, but may be longitudinally fixed between distal and proximal check elements 486, 488 respectively. Occluder 325 is free to rotate about the supporting steerable guidewire comprising, inter alia, shaft 144 and core wire 342, because transition sleeve 270, with occluder distal end 327 fixed thereto also is rotatable about the steerable guidewire. Of course, the inverse description may be more clinically significant, i.e., the steerable guidewire can be rotated freely within occluder 325, whether occluder 325 is in the deployed configuration or the collapsed configuration.

During use of occluder guidewire 320, occluder 325 may be collapsed by advancing core wire 342 distally through shaft 144 and transition sleeve 270 until proximal stop 481 engages distal stop 482, as shown in FIG. 13. Continued advancement of core wire 442 through shaft 144 will draw sleeve 270 along, but preferably not off, the distal portion of hollow shaft 144. The relative longitudinal movement of sleeve 270 with respect to shaft 144 causes occluder distal end 327 to separate from occluder proximal end 329, thus transforming occluder 325 from an expanded configuration to a collapsed configuration. Reversing the above manipulation, i.e., drawing core wire 342 proximally through shaft 144 permits occluder 325 to expand itself. Self-expansion of occluder 325 will stop when one of several conditions is met, similar to the description above with respect to self-expanding filter 25 of filter guidewire 220. Thereafter, continued withdrawal of core wire 342 will draw its distal end proximally within transition sleeve 270, creating axial separation (not shown) between stops 481, 482, thereby allowing the distal end of transition sleeve 270, with distal stop 482, to slide freely along distal tip member 43. Thus, in the deployed configuration of occluder guidewire 420, occluder 325 can self-expand or self-adjust its apposition with the vessel wall.

The arrangement shown in FIG. 13 provides unlimited rotation of shaft 144 and core wire 342 within occluder 325. Proximal thrust bearing 489 is of the cylindrical, plain, anti-friction type and is disposed about shaft 144 between slip ring 487 and distal check element 486. Proximal thrust bearing 489 serves to reduce friction between slip ring 487 or occluder proximal end 329 and distal check element 486, thus facilitating rotation of shaft 144 within occluder 325, especially when occluder 325 is being forced into the collapsed configuration by the push-pull manipulations described above regarding occluder guidewire 320. Proximal thrust bearing 489 may comprise a ring of low-friction material such as a fluoropolymer, a polyamide, HDPE or polyimide/fluoropolymer composite tubing as discussed above regarding liners 145, 145' and 145". Alternatively, proximal thrust bearing 489 may comprise a solid ring having a slippery coating applied thereto. Proximal thrust bearing 489 may be freely situated in the described location, or it may be fixed to any of the adjacent components such as shaft 144, occluder proximal end 329, distal check element 486 or slip ring 487. Another advantageous embodiment of the inventive apparatus has both proximal thrust bearing 489 and a distal thrust bearing (not shown) disposed between stops 381, 382.

FIG. 14 depicts a steerable distal protection guidewire apparatus having a deflectable distal region. Steerable protection guidewire 620 includes core wire 642 and flexible tubular tip member 43 fixed around the distal end of core wire 642. Hollow shaft 644 is movably disposed around core wire 642, and tubular protection element 625 is positioned concentrically with distal region 647 of core wire 642. Filter distal end 627 is coupled to tip member 43, and filter proximal end 629 is coupled near the distal end of shaft 644. Steerable protection guidewire 620 is shown with tubular protection element 625 in the deployed configuration.

FIG. 15 depicts steerable protection guidewire 620, wherein core wire 642 has been translated distally through hollow shaft 644 a sufficient distance to transform tubular protection element 625 from a first, deployed configuration, as shown in FIG. 14, into a second, collapsed configuration. FIG. 16 depicts steerable protection guidewire 620, wherein core wire 642 has been translated farther distally through hollow shaft 644 a sufficient distance to transform tubular protection element 625 from the second, collapsed configuration, as shown in FIG. 15, into a third, collapsed and curved configuration. In the second, collapsed configuration, distal movement of core wire 642 within hollow shaft 644 induces a longitudinal compression or compressive stress in core wire 642 and a longitudinal tension or tensile stress in the axially coupled combination of hollow shaft 644 and protection element 625. If tubular protection element 625 is disposed eccentrically about the distal region of core wire 642, the parallel but opposing stresses create a force couple that causes the two elements to deflect together. The inventors have discovered that, if tubular protection element 625 is disposed concentrically about the distal region of core wire 642 such that the opposing tensile and compressive stresses are coaxially aligned, even then tubular protection element 625 takes on axial curvature and deflects the underlying distal region of core wire 642.

FIG. 17 illustrates the mechanics of forming a curve in tubular protection elements in accordance with the invention. As in the alternate embodiment discussed above in connection with filter 25 and occluder 325, tubular protection element 625 incorporates material supporting struts 624, 624', which are arranged longitudinally as segments or sectors of a hollow cylinder to provide a tubular support structure for protection element 625. When axial tension is applied to tubular protection element 625 in the concentric construction described with respect to steerable protection guidewire 620, the tensile stress is uniformly distributed among struts 624, 624'. However, if strut 624' possesses a physical property different from struts 624, then strut 624' undergoes strain differently from struts 624, resulting in curvature of the tubular protection element 625. For example, if strut 624' has a modulus of elasticity lower than that of struts 624, then strut 624' will undergo greater strain or elongation than will struts 624 under equally-distributed stress conditions. The uneven elongation of struts 624, 624' results in curvature of tubular protection element 625 away from strut 624'.

Conversely, if strut 624' has a modulus of elasticity greater than that of struts 624, then strut 624' will undergo less strain or elongation than will the struts 624 under equal stress conditions, and the uneven elongation of struts 624, 624' results in curvature of protection element 625 towards strut 624'. The curve-forming variation between struts is not limited to material properties, but can relate to dimensional differences of struts or the spacing between struts.

Tubular protection elements such as the braided structures of filter 25 and occluder 325 may not include struts 624, 624'. However, such braided tubular protection elements have been found to exhibit curvature when placed under uniformly distributed tension. Thus, for purposes of analysis, a braided tubular protection element may be considered to comprise a hollow cylinder divided into elongate segments or sectors corresponding to struts 624, 624'.

Transforming a tubular protection element from the second, straight collapsed configuration to the third, curved and collapsed configuration requires translating the core wire distally within the hollow shaft, as discussed above. To adjust and maintain the relative longitudinal and/or rotational positions of core wires and the surrounding hollow shafts in the various embodiments of the invention, a removable handle device (not shown) of a type familiar to those of skill in the art may be used. Such handle devices can have telescoping shafts with collet-type clamps that grip respectively the core wires and shafts in the various embodiments of guidewire apparatuses according to the present invention. The handle device can also serve as a steering handle, or "torquer" which is useful for rotating small-diameter steerable-type guidewires that may be incorporated in the instant invention. Using such a handle device, a tubular protection element and underlying core wire region can controllably reach angle of deflection α in the range of 0-90 degrees from a longitudinal axis of the steerable distal protection guidewire. Alternatively, a desired range for angle of deflection α may be only 0-35 degrees from a longitudinal axis of the guidewire.

As discussed above, in order to steer a guidewire in accordance with the invention through tortuous vasculature, tip member 43 is typically bent or curved prior to insertion of the device. It may be useful for the clinician to combine a curved tip member 43 with a deflectable distal region. Even though the tubular protection element may be coupled in such a way that the core wire may rotate there within, the curvature of the tubular protection element will define the deflection angle of the distal region, regardless of the relative angular orientation of the core wire. Thus, bent tip member 43 may be oriented in any angular position relative to the deflectable distal region to create "S" curves, out-of-plane curves, and other complex three-dimensional curves while the guidewire is indwelling in the patient.

A method of using of a steerable distal protection guidewire apparatus 620 of the invention is described as follows. It should be noted that the example described below is unnecessarily limited to a filter guidewire embodiment. Steerable guidewire apparatus 620, having self-expanding tubular protection element 625 and hollow shaft 644 is provided, and advancing core wire 642 through shaft 644 collapses tubular protection element 625. With tubular protection element 625 in the collapsed configuration, filter guidewire 620 is introduced into the patient's vasculature. Advancing core wire 642 farther through shaft 644 causes collapsed self-expanding tubular protection element 625 to curve and deflect the underlying distal region of core wire 642. Steerable guidewire apparatus 620 can be negotiated through the patient's vessels by rotating and advancing the deflected distal region of the apparatus until tubular protection element 625 is beyond intended treatment site 15. Withdrawal of core wire 642 allows collapsed tubular protection element 625 to straighten as desired to aid in passage of steerable guidewire apparatus 620 through the patient's vessels. Farther withdrawal of core wire 642 allows tubular protection element 625 to expand. With tubular protection element 625 deployed into apposition with the vessel wall, a therapeutic catheter is advanced over steerable guidewire apparatus 620 to treatment site 15, and therapy, such as balloon angioplasty, is performed. Any embolic debris generated during the therapy is captured in tubular protection element 625. After the therapy is completed, the therapeutic catheter is prepared for withdrawal, as by deflating the balloon, if so equipped. Advancing core wire 642 through shaft 644 collapses tubular protection element 625. Finally, steerable guidewire apparatus 620 and the therapeutic catheter can be withdrawn separately or together, along with collected embolic debris contained within tubular protection element 625. If an occluder guidewire of the invention were used instead of a filter guidewire in the above-described method, then aspiration of trapped embolic material would be performed with a separate catheter before collapsing the occluder element.

One benefit of the structures of filter guidewires 20, 120 and 220 is that guidewire tip member 43 forms a fixed length tip of the device, regardless of the configuration of filter 25. Conversely, in occluder guidewire 320, the tip length changes as occluder distal end 327 slides along tip member 43 during transformation of occluder 325 between expanded and collapsed configurations. The variable tip length of occluder guidewire 320 provides a short tip when occluder 325 is collapsed, but the tip needs to lengthen distally of treatment site 15, if possible, during expansion of occluder 325. During deployment of filter guidewires 20, 120 and 220, the distal tip position of the device can remain fixed relative to treatment site 15. This is accomplished by the user holding core wires 42, 142 or 242 anchored relative to the patient, while applying tension to shafts 44 or 144 in the proximal direction. Filter 25 can be maintained in a collapsed configuration by a friction mechanism including bends 160, or by applying proximal tension to shafts 44, 144, thus holding filter proximal end 29 apart from filter distal end 27. Releasing the tension on shafts 44, 144, or advancing them manually, allows filter 25 to expand by filter proximal end 29 translating distally towards filter distal end 27. During this filter deployment, however, the distal tip does not need to move relative to filter 25 or treatment area 15.

While the invention has been particularly shown and described with reference to the preferred embodiments thereof, it will be understood by those skilled in the art that various changes in form and detail may be made there in without departing from the spirit and scope of the invention. For example, the invention may be used in any intravascular treatment utilizing a guidewire and wherein the possibility of loosening emboli exists. Although the description herein illustrates angioplasty and stent placement procedures as significant applications, it should be understood that the present invention is in no way limited to those environments.

We claim:

1. A method of steering a distal protection guidewire apparatus through a patient's tortuous vessel comprising:
   providing a guidewire apparatus having a hollow shaft, a core wire slidably disposed there through, and a tubular protection element disposed about a distal region of the apparatus;
   translating the core wire distally with respect to the hollow shaft to collapse the tubular protection element about the distal region of the apparatus;
   introducing the guidewire apparatus into the patient's vessel;
   translating the core wire distally with respect to the hollow shaft to deflect the collapsed tubular protection element and the distal region of the apparatus; and
   negotiating the guidewire apparatus through the patient's tortuous vessels by rotating and advancing the deflected distal end of the apparatus.

2. The method of steering a distal protection guidewire apparatus according to claim 1, further comprising:
   translating the core wire proximally with respect to the hollow shaft to straightening the collapsed tubular protection element and the distal region of the apparatus.

3. The method of steering a distal protection guidewire apparatus according to claim 1, further comprising:
   translating the core wire proximally with respect to the hollow shaft to deploy the tubular protection element into apposition with an interior site of the patient's vessel.

4. The method of steering a distal protection guidewire apparatus according to claim 1 wherein translating the core wire distally with respect to the hollow shaft comprises:
   applying axial tension to the tubular protection element; and
   applying axial compression to the core wire.

5. The method of steering a distal protection guidewire apparatus according to claim 1 wherein the tubular protection element is a filter.

6. The method of steering a distal protection guidewire apparatus according to claim 1 wherein the tubular protection element is an occluder.

* * * * *